United States Patent [19]
Chou et al.

[11] Patent Number: 5,433,891
[45] Date of Patent: * Jul. 18, 1995

[54] IMINOALCOHOL-OXAZOLIDINE MIXTURES AND THEIR USE

[75] Inventors: Chih-Yueh Chou, Elk Grove; Pattabbi K. Raman, Hawthorn Woods; Robert E. Malocha, Barrington; Thomas L. Johnson, Des Plaines; Vincent Nocito, Buffalo Grove; Marina D. Hoffman, Cary; Patrick E. Brutto, Norridge, all of Ill.

[73] Assignee: Angus Chemical Company, Buffalo Grove, Ill.

[ * ] Notice: The portion of the term of this patent subsequent to Jul. 12, 2011 has been disclaimed.

[21] Appl. No.: 220,825

[22] Filed: Mar. 31, 1994

Related U.S. Application Data

[63] Continuation-in-part of Ser. No. 866,662, Apr. 8, 1992, Pat. No. 5,328,635, which is a continuation-in-part of Ser. No. 745,476, Aug. 15, 1991, Pat. No. 5,223,174.

[51] Int. Cl.$^6$ .................. B01D 17/00; B01D 19/04; C09K 3/00
[52] U.S. Cl. ..................... 252/321; 252/194
[58] Field of Search ............... 252/194, 321, 392, 394, 252/315.1, 311, 358

[56] References Cited

U.S. PATENT DOCUMENTS

| | | | |
|---|---|---|---|
| 2,737,491 | 3/1956 | Hughes | 252/8.55 |
| 3,743,626 | 7/1973 | Emmons | 260/77.5 AQ |
| 3,941,753 | 3/1976 | Brinkmann | 260/77.5 MA |
| 4,115,169 | 9/1978 | Emmons | 156/71 |
| 4,192,786 | 3/1980 | Shibayama et al. | 260/18 EP |

(List continued on next page.)

FOREIGN PATENT DOCUMENTS

| | | |
|---|---|---|
| 0149765 | 7/1985 | European Pat. Off. |
| 3019356 | 11/1981 | Germany |
| 263216 | 11/1987 | Japan |

*Primary Examiner*—Robert L. Stoll
*Assistant Examiner*—Joseph D. Anthony

[57] ABSTRACT

Methods of using a mixture as a corrosion inhibitor, moisture or formaldehyde scavenger, reactive diluent, rheological modifier, thermoplastic foam inhibitor, antifreezing agent, decolorizing agent, drying agent, agent for reducing bubble formation, and an agent for reducing downglossing. The mixture consists of from 0 to 100 mole percent of an iminoalcohol compound:

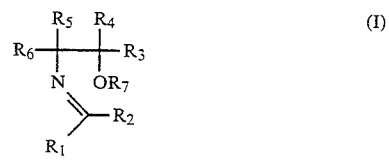

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of an oxazolidine compound having the structure:

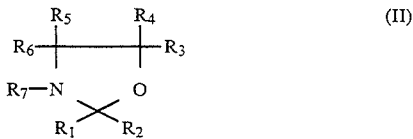

2 Claims, 2 Drawing Sheets

U.S. PATENT DOCUMENTS

| | | | |
|---|---|---|---|
| 4,316,875 | 2/1982 | Barth | 422/133 |
| 4,356,330 | 10/1982 | Cuscurida et al. | 568/756 |
| 4,443,577 | 4/1984 | Higgins | 524/590 |
| 4,504,647 | 3/1985 | Zabel et al. | 528/68 |
| 4,582,543 | 4/1986 | Bretz | 148/6.15 R |
| 4,770,803 | 9/1988 | Forsberg | 252/75 |
| 5,104,955 | 4/1992 | Mathai | 526/323.2 |
| 5,223,174 | 6/1993 | Chou et al. | 252/194 |
| 5,264,148 | 11/1993 | Chou et al. | 252/194 |

IMINOALCOHOL-OXAZOLIDINE MIXTURES AND THEIR USE

CROSS-REFERENCE TO RELATED APPLICATIONS

This application is a continuation-in-part of patent application Ser. No. 07/866,662, filed Apr. 8, 1992, now U.S. Pat. No. 5,328,635 which is in turn a continuation-in-part of application Ser. No. 07/745,476, filed Aug. 15, 1991, which issued as U.S. Pat. No. 5,223,174, on Jun. 29, 1993.

FIELD OF THE INVENTION

The present invention is generally related to methods of using iminoalcohol-oxazolidine mixtures. In particular, the present invention relates to methods of using the mixtures as a formaldehyde scavenger, reactive diluent, rheological modifier, antifreezing agent, decolorizing agent, drying agent, bubble formation inhibitor or an agent to reduce downglossing.

BACKGROUND OF THE ART

Coating, adhesive or sealant formulations may include rheological modifiers to reduce viscosity, disperse pigments and improve solvency and flow. Formulations which do not contain rheological modifiers may exhibit a rapid increase in viscosity for a relatively small increase in solids content. The increased viscosity causes the formulation to set quickly resulting in striations in the formulation. Addition of a rheological modifier enables the formulation to flow into a smooth layer before it sets. Conventional rheological modifiers include polyethylene glycols such as Carbowax and polyethylene oxides such as Polyox.

There is a need for a rheological modifier to reduce viscosity and volatile organic content, disperse pigments, and improve the solvency and flow properties of a coating, adhesive or sealant.

Radiation curable coatings are generally composed mainly of radiation curable multifunctional monomers, oligomers and polymers. Restrictions on solvent content in the atmosphere have increased efforts to provide radiation curable coatings which do not contain any volatile components, but instead include components which form either the whole or a part of the hardened film itself. Reactive diluents are used to lower the volatile content of the coatings by reducing the loss of organic solvents into the atmosphere. Reactive diluents are compounds of low volatility which reduce the viscosity of a coating, adhesive or sealant formulation and become a permanent part of the formulation through chemical reaction. Accordingly, reactive diluents are added to radiation curable coatings not only as a diluent, but to reduce viscosity, copolymerize with the oligomers and polymers to form a part of the coating, and contribute to the final properties of the cured film. Examples of reactive diluents for use in coatings are monofunctional acrylic monomers, multifunctional acrylates and methacrylates of alkoxylated and non-alkoxylated polyols such as trimethylolpropane triacrylate, trimethylolpropane trimethacrylate, pentaerythritol triacrylate and 1,6-hexanediol diacrylate and dimethacrylate, difunctional diluents such as 1,6-hexanediol diacrylate and dimethacrylate, and trifunctional diluents such as trimethylolpropane triacrylate and pentaerythritol triacrylate. These reactive diluents pose problems which limit their use in radiation curable coatings. The diluents are known to produce brittle films with severe shrinkage and poor adhesion to substrates, exhibit slow cure response or poor solvency effects, ineffectively reduce viscosity, or cause serious skin irritancy problems.

There is a need for a reactive diluent which exhibits good cure response, low intrinsic viscosity, low film shrinkage, and excellent solvating or viscosity reducing properties.

Formaldehyde is a raw material frequently used in polymeric systems including phenol-formaldehyde, urea-formaldehyde, and melamine-formaldehyde. Exposure to formaldehyde vapors in the workplace is stringently controlled by the use of formaldehyde scavengers. Formaldehyde scavengers capture formaldehyde and hold it in a form having significantly lower formaldehyde vapor pressure. Products such as textiles and plywood typically contain a formaldehyde scavenger to reduce free formaldehyde levels without changing the physical properties of the products. Known formaldehyde scavengers include nitroparaffins such as nitromethane (NM TM), nitroethane (NE TM), 1-nitropropane (NiPar S-10 TM) and 2nitropropane (NiPar S-20 TM), and amino alcohols such as 2-amino-2-methyl-1propanol (AMP TM), 2-amino-2-ethyl-1,3-propanediol (AEPD®) and tris(hydroxymethyl)aminomethane (TRIS AMINO®), which are manufactured by ANGUS Chemical Company.

There is a need for a formaldehyde scavenger which efficiently, cost effectively, and safely removes formaldehyde from polymeric systems and from any other preparation where free formaldehyde is a problem, without seriously detracting from the performance or physical properties of the system.

Phenol-based peroxide inhibitors have been suggested as a substitute for 2,6-di-t-butyl-p-cresol for use in polyol formulations because of the limited supply of the conventional p-cresol inhibitor. However, the phenol-based inhibitors cause discoloration of the polyol. N-(2-hydroxyalkyl)oxazolidines are known decolorizing agents for removing color-forming bodies from a mixture of alkyl substituted phenols.

There is a continuing need for a decolorizing agent which removes the color from a phenol, amine or other discolored preparation.

Urethane coatings when cured often contain bubbles and pinholes. These bubbles and pinholes occur because moisture in the coating reacts with isocyanate during the curing process.

There is a need for an additive that reduces formation of bubbles and pinholes in urethane coatings.

When urethane coatings are applied under conditions of high temperature and humidity, a phenomenon called downglossing often occurs. Downglossing is caused by the reaction of humidity (water) with isocyanate, resulting in microbubbles on the surface which reduce gloss.

There is a need for an additive that reduces downglossing in urethane coatings by inhibiting the formation of bubbles on the surface of the urethane coating.

SUMMARY OF THE INVENTION

The present invention provides a method of scavenging formaldehyde from a preparation by admixing with the preparation an effective amount of a mixture consisting of:

from 0 to 100 mole percent of the compound:

(I)

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of the compound:

(II)

wherein: $R_1$, $R_2$, $R_3$, $R_4$, $R_5$, $R_6$ and $R_7$ are as defined above for compound (I). An effective amount or the mixture including at least one of the formaldehyde scavenging compounds (I) and (II) described above is intimately admixed with the preparation. In a preferred embodiment, the formaldehyde scavenging compound is at least one of a ketimine or aldimine alcohol of compound (I) and an oxazolidine compound (II) and the effective amount of the mixture includes from 1 to about 100 moles or the mixture for every mole of formaldehyde in the preparation.

Another aspect of the present invention is a method of reducing volatile organic content and concentration of an active material in a preparation and improving rheological properties of the preparation using a reactive diluent. An effective amount of the mixture including at least one of the reactive diluent compounds (I) and (II) described above is admixed with the preparation. Preferably, from 1 to about 50 wt. % of the mixture is added based on the total weight of the preparation.

Yet another aspect of the present invention is a method of modifying the theology of a preparation. An effective amount of the mixture including at least one of the rheological modifier compounds (I) and (II) described above is admixed with the preparation. Preferably, from 1 to about 50 wt. % of the mixture is added based on the total weight of the preparation.

Still another aspect of the invention is directed to a method for preventing the formation of ice crystals and for depressing the freezing point of a preparation. According to the method, an effective amount of the mixture including at least one of the antifreeze compounds (I) and (II) described above is intimately admixed with the preparation. The preparation is preferably an industrial fluid. In a preferred embodiment, the moisture scavenging compound is at least one of a ketimine or aldimine alcohol of compound (I) and an oxazolidine compound (II) and the effective amount of the mixture includes from 1 to 100 moles of the mixture for every mole of water in the preparation. If the preparation does not contain water, the effective amount of the mixture is from 1 to about 50 wt. % of the mixture based on the total weight of the preparation.

Another aspect of the present invention is a method of obtaining a stable dispersion, suspension or solution. An effective amount of the mixture including at least one of the stabilizing compounds (I) and (II) described above is admixed with the dispersion, suspension or solution. Preferably, from 1 to about 50 wt. % of the mixture is added based on the total weight of the dispersion, suspension or solution.

Still another aspect of the present invention is a method of reducing bubble formation in urethane coatings. An effective amount of the mixture including at least one of the compounds (I) and (II) described above is admixed with the urethane. Preferably, from about 1 to about 50 wt. % of the mixture is added based on the total weight of the coating.

In another aspect, the present invention provides a method of reducing downglossing in urethane coatings. As used herein, the term "downglossing" describes the phenomenon known as "dieback" in the art. An effective amount of the mixture including at least one of the compounds (I) and (II) described above is admixed with the urethane. Preferably, from about 1 to about 50 wt. % of the mixture is added based on the total weight of the coating.

BRIEF DESCRIPTION OF THE FIGURES

In the Figures, which form a portion of the Specification.

DETAILED DESCRIPTION OF THE INVENTION

The present invention provides a mixture which can be advantageously used in the formulation of specialty polyurethane systems including sealants, adhesives and coatings. For the purposes of the present invention, a coating is any polyurethane coating, including both one and two component coatings. These coatings are typically cured by moisture, ambient, thermal, forced dry, radiation or bake curing. The mixture acts as a rheological modifier, drying agent, decolorizing agent, dispersant, reactive diluent and bubble formation inhibitor in these systems. Additionally, the mixture is a reactive diluent in inks, a drying agent in inks, composites, sacrificial pigments, radiation cure coatings and industrial gasses, an antifreezing agent in functional fluids, and a formaldehyde scavenger in preparations such as polymeric systems, textiles and plywood.

It has been discovered that a class of compounds including ketimine and aldimine alcohols and substituted monocyclic oxazolidines are excellent formaldehyde scavengers, decolorizing agents, drying agents, reactive diluents, antifreezing agents, dispersants, rheological modifiers, and bubble formation inhibitors. The prior art has disclosed a rather broad class of oxazolidine compounds as crosslinking reagents, reacting with polyfunctional isocyanates in the presence of polyols or water to form polymeric coatings. U.S. Pat. No. 4,101,527 discloses an equimolar reaction of an oxazolidine with a polyfunctional isocyanate in the presence of water to form a polyurethane coating. U.S. Pat. No. 3,941,753 describes pre-polymers for coating formation prepared from the reaction of a ketiminoalkanol with a polyisocyanate. Bicyclic moisture scavenging oxazolidine compounds for use in formulating polyurethane coatings are disclosed in copending U.S. patent application Ser. No. 07/624,062 by Chou, et al., entitled "Moisture Scavenging Oxazolidines", filed Dec. 4, 1990.

The mixture of the present invention consists of from 0 to 100 mole percent of an iminoalcohol compound:

(I)

wherein: $R_1$ is a methyl or methylol group, an ethyl or ethylol group, a branched or straight chain alkyl or alkanol group, a cycloalkyl group, or an aryl group; $R_2$ is a hydrogen atom, a methyl or methylol group, an ethyl or ethylol group, a straight chain or branched chain alkyl or alkanol group, a cycloalkyl group, or an aryl group, or $R_1$ and $R_2$ are fused together with the attached carbon to form a cycloalkane ring; $R_3$, $R_4$ and $R_5$ are, individually, a hydrogen atom, a methyl or methylol group, an ethyl or ethylol group, or a straight chain or branched chain alkyl or alkanol group; $R_6$ is a hydrogen atom, a methyl group, an ethyl group, or a straight chain or branched chain alkyl group; and $R_7$ is a hydrogen atom, a methyl or methylol group, an ethyl or ethylol group, a straight chain or branched chain alkyl or alkanol group, a cycloalkyl group, an acyl group, an aryl group, an ester containing group, or an amino containing group; and from 0 to 100 mole percent of an oxazolidine compound:

(II)

wherein: $R_1$, $R_2$, $R_3$, $R_4$, $R_5$, $R_6$ and $R_7$ are as defined above for compound (I).

In one preferred embodiment of the invention, the $R_7$ substituent is a hydrogen atom, a methyl group, an ethyl group, a straight chain or branched chain alkyl group, an acyl group, an aryl group, an ester containing group, or an amino containing group; the $R_6$ substituent of the compound is a hydrogen atom or a methyl group; the $R_5$ substituent of the compound (I) is a hydrogen atom, a methyl or ethyl group, or a ($C_3$–$C_5$) branched chain or straight chain alkyl group; the $R_3$ and $R_4$ groups are, individually, hydrogen atoms or methyl groups; the $R_1$ substituent is an aryl group, an ethyl group or a ($C_3$–$C_5$) branched or straight chain alkyl group; and the $R_2$ substituent is a hydrogen atom, a methyl group, an ethyl group, or a ($C_3$–$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$–$C_5$) branched or straight chain alkyl group; the $R_2$ and $R_5$ substituents are methyl or ethyl groups, or ($C_3$–$C_5$) branched or straight chain alkyl groups; the $R_7$ substituent is a hydrogen atom, a methyl group, an ethyl group, an acyl group, an aryl group, an ester containing group, or an amino containing group; the $R_3$ and $R_4$ groups are, individually, hydrogen atoms or methyl groups; and the $R_6$ group is a hydrogen atom. Most preferably, the $R_1$ substituent is an aryl group or a ($C_3$–$C_5$) branched or straight chain alkyl group; the $R_2$ substituent is a methyl group, an ethyl group, or a ($C_3$–$C_5$) branched or straight chain alkyl group; the $R_5$ group is a methyl group or an ethyl group; the $R_3$ and $R_4$ groups are, individually, hydrogen atoms or methyl groups; the $R_7$ group is a hydrogen atom, an ethyl group, or an amino containing group; and the $R_6$ group is a hydrogen atom.

The preferred R group substituents of the ketimine or aldimine alcohol compounds (I) of the present invention are also those which increase the reactivity of the compound to formaldehyde. The formaldehyde scavenging ketimine or aldimine alcohol compounds (I) of the present invention can react with formaldehyde and upon hydrolysis, will react with formaldehyde to form an oxazolidine reaction product. One mole of formaldehyde scavenging ketimine or aldimine alcohol will react with and remove one mole of formaldehyde. Therefore, it is preferred that the formaldehyde scavenging mixtures of the invention containing ketimine or aldimine alcohols include at least one mole of the formaldehyde scavenging ketimine or aldimine alcohol for each mole of formaldehyde to be removed from a preparation. However, since a perfectly efficient reaction environment cannot be guaranteed in industrial settings, it is preferable that from 1 to about 10 moles of the formaldehyde scavenging ketimine or aldimine alcohol be included for every mole of formaldehyde to be removed from a preparation. Some applications require that only from 1 to about 3 moles of the formaldehyde scavenging ketimine or aldimine alcohol be included for every mole of formaldehyde to be removed from the preparation. Greater amounts of the ketimine or aldimine alcohol can be added to reduce the viscosity and/or volatile organic content of the preparation. As much as 100 moles of the mixture may be required to effect the desired change in the physical properties of the preparation.

In one preferred embodiment of the invention, the $R_7$ substituent of the compound (II) is a hydrogen atom, a methyl group, an ethyl group, a straight chain or branched chain alkyl group, an acyl group, an aryl group, an ester containing group, or an amino containing group; the $R_6$ substituent of the compound is a hydrogen atom or a methyl group; the $R_5$ substituent of the compound is a hydrogen atom, a methyl or ethyl group, or a ($C_3$–$C_5$) branched chain or straight chain alkyl group; the $R_3$ and $R_4$ groups are hydrogen atoms; the $R_1$ substituent is an aryl group, an ethyl group or a ($C_3$–$C_5$) branched or straight chain alkyl group; and the $R_2$ substituent is a hydrogen atom, a methyl group, an ethyl group, or a ($C_3$–$C_5$) branched or straight chain alkyl group, or $R_1$ and $R_2$ are fused together with the attached carbon to form a cycloalkane ring. More preferably, the $R_1$ substituent is an aryl group, an ethyl group or a ($C_3$-$C_5$) branched or straight chain alkyl group; the $R_2$ and $R_5$ substituents are methyl or ethyl groups, or ($C_3$-$C_5$) branched or straight chain alkyl groups; the $R_7$ substituent is a hydrogen atom, a methyl group, an ethyl group, an acyl group, an aryl group, an ester containing group, or an amino containing group; the $R_3$ and $R_4$ groups are, individually, hydrogen atoms or methyl groups; and the $R_6$ group is a hydrogen atom. Most preferably, the $R_1$ substituent is an aryl group or a ($C_3$-$C_5$) branched or straight chain alkyl group; the $R_2$ substituent is a methyl group, an ethyl group, or a ($C_3$-$C_5$) branched or straight chain alkyl group; the $R_5$ group is a methyl group or an ethyl group; the $R_3$ and $R_4$ groups are, individually, hydrogen atoms or methyl groups; the $R_7$ group is a hydrogen atom, an ethyl group, or an amino containing group; and the $R_6$ group is a hydrogen atom.

The preferred R group substituents of the oxazolidine compounds (II) of the present invention are also those which increase the reactivity of the compound to formaldehyde. The formaldehyde scavenging oxazolidine compounds (II) of the present invention react with formaldehyde when the $R_7$ substituent is a hydrogen atom. The reaction occurs regardless of the presence of water in the preparation from which the formaldehyde is to be removed. It is preferable that from 1 to about 10 moles of the formaldehyde scavenging oxazolidine be included for every mole of formaldehyde to be removed from a preparation. Some applications require that only from 1 to about 3 moles of the moisture scavenging oxazolidine be included for every mole of water to be removed from the preparation. Greater amounts of the oxazolidine can be added to reduce the viscosity and/or volatile organic content of the preparation. As much as 100 moles of the mixture may be required to effect the desired change in the physical properties of the preparation.

The structure of the R substituents in either the ketiminoalkanols, aldiminoalkanols or monocyclic oxazolidines is determined by the selection of the reactant precursor compounds. Reaction of a primary amino alcohol with a carbonyl compound produces an equilibrium mixture of an oxazolidine compound (II) along with its tautomeric iminoalcohol compound (I) as confirmed by IR spectral dam. The amount of each compound present in the equilibrium mixture varies depending on the R substituents. Bulky substituents at $R_1$ and $R_2$, as well as substitution at $R_3$ and $R_4$ will generally shift the equilibrium to the iminoalcohol compound (I), although the compounds of the present invention are not limited thereto. In a specific embodiment of the invention, the 2-(1-hydroxybutyl) (4-methyl-2-pentylidine) amine/4-ethyl-2-methyl-2-(2-methylpropyl)- 1,3-oxazolidine iminoalcohol-oxazolidine mixture is prepared by reacting D,L-2-amino-1-butanol with methyl isobutyl ketone.

One aspect of the invention is directed to a method of scavenging formaldehyde from a preparation. In one embodiment, the preparation is a phenol-formaldehyde, urea-formaldehyde, or melamine-formaldehyde polymeric system. According to the method, an effective amount of the mixture of the present invention including a ketimine or aldimine alcohol and/or a monocyclic oxazolidine formaldehyde scavenging compound as described above is intimately admixed with the preparation. An effective amount is an amount of the mixture which removes free formaldehyde in the preparation. In a preferred embodiment, the effective amount includes from 1 to about 10 moles of the mixture for every mole of formaldehyde in the preparation. Most preferably, from 1 to about 3 moles of the mixture is added to the preparation for every mole of formaldehyde in the preparation. The compounds of the present invention will scavenge formaldehyde regardless of the presence of water in the preparation. However, the presence of a catalyst or water may facilitate the reaction of the oxazolidine compound with formaldehyde.

Another aspect of the present invention is directed to a method for preventing the formation of ice crystals and for lowering the freezing point of an industrial fluid while removing moisture from the preparation. Conversely, conventional antifreezing agents lower the freezing point of an industrial fluid without removing moisture from the fluid. According to the method of the invention, an effective amount of the mixture of the present invention including a ketimine or aldimine alcohol and/or a monocyclic oxazolidine compound as described above is intimately admixed with an industrial fluid which may be exposed to low temperatures during use in automobiles, airplanes or other machinery. An effective amount is an amount of the mixture which prevents an industrial fluid from freezing. The term "industrial fluid" is defined for the purposes of this invention to include any lubricant, hydraulic fluid, hydrocarbon fuel, jet fuel and the like. In a preferred embodiment, the effective amount includes from 1 to about 10 moles of the mixture for every mole of water in the industrial fluid. Most preferably, from 1 to about 3 moles of the mixture is added to the preparation for every mole of water in the industrial fluid. If the preparation does not contain water, the effective amount of the mixture is from 1 to about 30 wt. % of the mixture based on the total weight of the preparation. Most preferably, from 1 to about 10 wt. % of the mixture based on the total weight of the preparation is added to the preparation.

A further aspect of the present invention is directed to a method of reducing volatile organic content and concentration of an active material in a preparation and improving rheological properties of the preparation using a reactive diluent. An active material is a component of the preparation which is reactive with polyisocyanate or water. In one embodiment, the active material is a polyol or prepolymer which is a component of a coating, adhesive, sealant, epoxy, radiation cure coating, or ink preparation. The mixture of the present invention is substituted for the volatile organic solvents and reacts to form a part of the preparation. The mixture acts to form a high solids preparation while reducing the release of volatile organics into the atmosphere. According to the method, an effective amount of the mixture of the present invention including a ketimine or aldimine alcohol and/or a monocyclic oxazolidine reactive diluent compound as described above is intimately admixed with the preparation. An effective amount is an amount of the mixture sufficient to reduce the viscosity and volatile organic content of the preparation and provide an acceptable potlife or stability and cure rate while improving the film properties of the preparation. In a preferred embodiment, the effective amount includes from 1 to about 30 weight percent of the mixture based on the total weight of the preparation. Most preferably, from 1 to about 10 weight percent of the mixture based on the total weight of the preparation is added.

Film properties which may be improved by the mixture of the present invention include, but are not limited to, gloss, hardness, impact resistance, flexibility, chemical resistance, abrasion resistance, exterior durability, humidity and salt fog resistance.

Another aspect of the present invention is directed to a method of obtaining a stable dispersion, suspension or solution. According to the method, an effective amount of the mixture of the present invention including a ketimine or aldimine alcohol and/or a monocyclic oxazolidine stabilizing compound as described above is intimately admixed with the dispersion, suspension or solution. An effective amount is an amount of the mixture which provides sufficient solvency or pigment dispersability. Solvency is the ability of an additive to hold a resin or other binder in solution. Dispersability is the ability of an additive to increase the stability of a suspension of pigments in a liquid medium. In a preferred embodiment, the effective amount includes from 1 to about 30 weight percent of the mixture based on the total weight of the dispersion, suspension or solution. Most preferably, from 1 to about 10 weight percent of the mixture based on the total weight of the dispersion, suspension or solution is added.

A further aspect of the invention is directed to a method of modifying the rheology of a preparation. Rheology is the deformation and flow of the preparation. Rheological properties which may be modified by the mixture of the present invention include sagging, flow and film build. In an embodiment of the method, the preparation is a coating, adhesive or sealant which has improved flow and film properties as a result of reduced viscosity. According to the method, an effective amount of the mixture of the present invention including a ketimine or aldimine alcohol and/or a monocyclic oxazolidine compound as described above is intimately admixed with the preparation. An effective amount is an amount of the mixture which is sufficient to reduce the viscosity and improve the rheological properties of the preparation. In a preferred embodiment, the effective amount includes from 1 to about 30 weight percent of the mixture based on the total weight of the preparation. Most preferably, from 1 to about 10 weight percent of the mixture based on the total weight of the preparation is added. Although the mixture can be added to the preparation at any stage, it is most common to add the mixture during the grind phase and/or the let down phase. When the mixture is added during the grind phase, the mixture also acts as a pigment dispersant to prevent agglomerate formation. Accordingly, addition of the mixture to a coating, adhesive or sealant assures that the pigment particles are finely divided and stabilized.

Another aspect of the invention is directed to a method of decolorizing a preparation. According to the method, an effective amount of the mixture of the present invention including a ketimine or aldimine alcohol and/or a monocyclic oxazolidine decolorizing compound as described above is intimately admixed with the preparation. An effective amount is an amount of the mixture which will sufficiently remove the color from a preparation. In a preferred embodiment, the effective amount includes from 1 to about 30 weight percent of the mixture based on the total weight of the preparation. Most preferably, from 1 to about 10 weight percent of the mixture based on the total weight of the preparation is added. The preparations which may be decolorized include phenols and amines.

Greater amounts of the mixture can be added in the methods of the present invention to reduce the viscosity and/or volatile organic content of the preparation. In excess of 100 moles of the mixture for every mole of water or formaldehyde in a preparation may be required to effect the desired change in the physical properties of the preparation. Likewise, in excess of 50 weight percent of the mixture based on the total weight of the preparation may be required in decolorant, antifreeze, reactive diluent or rheological modifier applications.

When water reacts with isocyanate within a preparation, it forms bubbles which create pinholes within the preparation. The mixtures of this invention can also be used to minimize the formation of bubbles in a coating. Bubbles have been visually eliminated from the coating, improving the film integrity by providing improved abrasion resistance and impact resistance.

When polyurethane coatings are applied under conditions of high humidity, a phenomenon known as downglossing (dieback) can occur. Downglossing is caused by the reaction of humidity (water) with isocyanate, resulting in microbubbles on the surface of the coating which reduce gloss. Downglossing affects air dry systems more severely than forced dry or baked systems. The iminoalcohol-oxazolidine mixtures of this invention can be used as additives for minimizing downglossing because these mixtures react with moisture more rapidly than does isocyanate.

The following examples are presented to describe preferred embodiments and utilities of the present invention and are not meant to limit the present invention unless otherwise stated in the claims appended hereto. Each of the equilibrium mixtures is referred to in the examples by the name of the iminoalcohol compound present in the mixture. These iminoalcohol compounds and their corresponding oxazolidines which form equilibrium mixtures are listed in the table below.

TABLE 1

| Iminoalcohol-Oxazolidine Mixtures of the Present Invention | |
|---|---|
| Iminoalcohol | Oxazolidine |
| 2-(1-hydroxybutyl) (cyclohexylidine) amine | 4-ethyl-1,3-oxazolidine-2-spiro-1'-cyclohexane |
| 2-(1-hydroxy-2-hydroxymethylbutyl) (cyclohexylidine) amine | 4-ethyl-4-hydroxymethyl-1,3-oxazolidine-2-spiro-1'-cyclohexane |
| 2-(1-hydroxybutyl) (4-methyl-2-pentylidine) amine | 4-ethyl-2-methyl-2-(2-methylpropyl)-1,3-oxazolidine |
| 2-(1-hydroxy-2-hydroxymethylbutyl) (4-methyl-2-pentylidine) amine | 4-ethyl-4-hydroxymethyl-2-methyl-2-(2-methylpropyl)-1,3-oxazolidine |
| 2-(1-hydroxybutyl) (1-phenyl-1-ethylidine) amine | 4-ethyl-2-methyl-2-phenyl-1,3-oxazolidine |
| 2-(1-hydroxy-2-hydroxymethylbutyl) (1-phenyl-1-ethylidine) amine | 4-ethyl-4-hydroxymethyl-2-methyl-2-phenyl-1,3-oxazolidine |
| 2-(1-hydroxybutyl) (2-heptylidine) amine | 4-ethyl-2-methyl-2-pentyl-1,3-oxazolidine |
| 2-(1-hydroxy-2-hydroxymethylbutyl) (2-heptylidine) amine | 4-ethyl-4-hydroxymethyl-2-methyl-2-pentyl-1,3-oxazolidine |
| 2-(1-hydroxybutyl) (5-methyl-2-hexylidine) amine | 4-ethyl-2-methyl-2-(3-methylbutyl)-1,3-oxazolidine |
| 2-(1-hydroxy-2-hydroxymethylbutyl) (5-methyl-2-hexylidine) amine | 4-ethyl-4-hydroxymethyl-2-methyl-2-(3-methylbutyl)-1,3-oxazolidine |
| 2-(1-hydroxybutyl) (2,6-dimethyl-4-heptylidine) amine | 2,2-(di-2-methylpropyl)-4-ethyl-1,3-oxazolidine |
| 2-(1-hydroxy-2-methylpropyl) (4-methyl-2-pentylidine) amine | 2-(2-methylpropyl)-2,4,4-trimethyl-1,3-oxazolidine |
| 2-(1,3-dihydroxy-2-methylpropyl) (4-methyl-2-pentylidine) amine | 4-hydroxymethyl-2,4-dimethyl-2-(2-methylpropyl)-1,3-oxazolidine |
| 1-(2-hydroxypropyl)(5-methyl-2- | 2,5-Dimethyl-2-(3-methyl- |

TABLE 1-continued

| Iminoalcohol-Oxazolidine Mixtures of the Present Invention | |
|---|---|
| Iminoalcohol | Oxazolidine |
| hexylidine) amine | butyl)-1,3-oxazolidine |
| | 3-ethyl-2-methyl-2-(3-methyl-butyl)-1,3-oxazolidine |

EXAMPLES

Example 1

Preparation of 2-(1-Hydroxybutyl)(cyclohexylidine) amine/4-Ethyl-1,3-oxazolidine-2-spiro-1'-cyclohexane Mixture D,L-2-Amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, cyclohexanone (161.9 grams; 1.6 mol.) was added over a ten minute period resulting in an exothermic reaction (26° C.→65° C.). The reaction mixture was heated to reflux and 24 grams of water were collected in the Dean-Stark trap over a two hour period. The product was purified by vacuum distillation (77°–78° C. @ 3.5 mm Hg) using a mirrored column (250 mm ×10 mm i.d.) packed with metal helixes. The material was stored under a nitrogen atmosphere.

Example 2

Preparation of 2-(1-Hydroxy-2-hydroxymethylbutyl)-(cyclohexylidine) amine/4-Ethyl-4hydroxymethyl-1,3-oxazolidine -2-spiro-1'-cyclohexane Mixture 2-Amino-2-ethyl-1, 3-propanediol (AEPD®) (178.9 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, cyclohexanone (309.1 grams; 3.1 mol.) was added over a seven minute period causing a lower reaction mixture temperature. The reaction mixture was heated to reflux and 25 grams of water were collected in the Dean-Stark trap over a two hour period. The product was purified by vacuum distillation (121° C.–123° C. @ 2 mm Hg) using a mirrored column (250 mm×10 mm i.d.) packed with metal helixes. The material was stored under a nitrogen atmosphere.

Example 3

Preparation of 2-(1-Hydroxymethylbutyl)(4-methyl-2-pentylidine) amine/4-Ethyl-2-methyl-2-(2-methylpropyl)-1,3-oxazolidine Mixture D,L-2-Amino-1-butanol (AB®) (133.7 grams; 1.5 mol.) was added to a 3-neck, 500 ml. round bottom flask equipped with a magnetic stir bar, a 250 ml addition funnel, a thermometer, and a Dean-Stark trap (50 ml capacity). While stirring, 4-methyl-2-pentanone (MIBK) (165.3 grams; 1.6 mol.) was added over a three minute period causing a lower reaction mixture temperature. (20° C.→17° C.). The reaction mixture was heated to reflux and 25 grams of water were collected in the Dean-Stark trap over a six hour period. The crude product was purified by vacuum distillation (91° C.@14 mm Hg) using a mirrored column (250 mm×10 mm i.d.) packed with metal helixes. The material was stored under a nitrogen atmosphere.

Example 4

Preparation of 2-(1-Hydroxy-2-hydroxymethylbutyl(4-methyl-2-pentylidine) amine/4-Ethyl-4-hydroxymethyl-2-methyl-2-(2methylpropyl)-1,3-oxazolidine Mixture 2-Amino-2-ethyl-l,3-propanediol (AEPD®) (179.3 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, 4-methyl-2-pentanone (MIBK) (315.7 grams; 3.1 mol.) was added over a three minute period causing the reaction mixture temperature to lower by 1° C. The reaction mixture was heated to reflux and 24 grams of water were collected in the Dean-Stark trap over a fifty-five hour period. The crude product was purified by vacuum distillation (107° C.–109° C.@2 mm Hg) using a mirrored column (250 mm×10 mm i.d.) packed with metal helixes. The material was stored under a nitrogen atmosphere.

Example 5

Preparation of 2-(1-Hydroxybutyl)(1-phenyl-1-ethylidine) amine/4-Ethyl-2-methyl-2-phenyl-1,3-oxazolidine Mixture D,L-2-Amino-1-butanol (AB®) (133.7 grams; 1.5 mol.) was added to a 3-neck, 500 ml round bottom flask equipped with a magnetic stir bar, a 250 ml. addition funnel, a thermometer, and a Dean-Stark trap (50 ml capacity). While stirring, acetophenone (198.3 grams; 1.6 mol.) was added over a five minute period causing a lower reaction mixture temperature (21° C.→18° C.). The reaction mixture was heated to reflux and 26 grams of water were collected in the Dean-Stark trap over a twenty hour period. The crude product was purified by a vacuum distillation (95°–99° C. @2–3 mm Hg) using a mirrored column (250 mm×10 mm i.d.) packed with metal helixes. The material was stored under a nitrogen atmosphere.

Example 6

Preparation of 2-(1-Hydroxy-2-hydroxymethylbutyl)(1-phenyl-1-ethylidine) amine/4-Ethyl-4-hydroxymethyl-2-methyl-2-phenyl-1,3-oxazolidine Mixture 2-Amino-2-ethyl-1,3-propanediol (AEPD®) (179.4 grams; 1.3 mol.) was added to a 3-neck, 1 liter round bottom flask equipped with a mechanical stirrer, a 500 ml addition funnel, a thermometer, and a Dean-Stark trap (100 ml capacity). While stirring, acetophenone (378.7 grams; 3.1 mol.) was added over an eight minute period causing a three degree lowering in the reaction mixture temperature. The reaction mixture was heated to reflux and 20 grams of water were collected in the Dean-Stark trap over a twenty hour period. The crude product was purified by vacuum distillation (114° C.→120° C.@0.9–1.0 mm Hg) using a mirrored column (250 mm×10 mm i.d.) packed with metal helixes. The material was stored under a nitrogen atmosphere.

Example 7

Preparation of 2-(1-Hydroxybutyl)(2-heptylidine) amine/4-Ethyl-2-methyl-2-pentyl-1.3-oxazolidine Mixture D,L-2-amino-1-butanol (AB®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 2-heptanone (MAK) (188.3 grams; 1.6 mol.) was added over a three minute period causing a lowering of the reaction mixture temperature (24° C.→20° C.). The reaction mixture was heated to reflux and 24 grams of water were collected in the Dean-Stark trap over a thirteen hour period. The crude product was purified by vacuum distillation (70°–73° C.@0.8–1.0 mm Hg) using a mirrored column (250 mm × 10 mm i.d.) packed with metal helixes. The material was stored under a nitrogen atmosphere.

Example 8

Preparation of 2-(1-Hydroxy-2-hydroxymethylbutyl)(2-heptylidene) amine/4-Ethyl-4-hydroxymethyl-2-methyl-2-pentyl-1,3-oxazolidine Mixture 2-Amino-2-ethyl-1,3-propanediol (AEPD ®) (179.3 grams; 1.3 mol.)was added to a 3-neck, 1 liter round bottom flask equipped with a mechanical stirrer, a 500 ml addition funnel, a thermometer, and a Dean-Stark trap (100 ml capacity). While stirring, 2-heptanone (MAK) (359.6 grams; 3.1 mol.) was added over a five minute period causing a two degree temperature drop in the reaction mixture temperature (24° C.→22° C.). The reaction mixture was heated to reflux and 26 grams of water were collected in the Dean-Stark trap over a thirteen hour period. The crude product was purified by vacuum distillation (97° C.–98° C.@1.0 mm Hg) using a mirrored column (250 mm × 10 mm i.d.) packed with metal helixes. The material was stored under a nitrogen atmosphere.

Example 9

Preparation of 2-(1-Hydroxybutyl)(5-methyl-2-hexylidine) amine/4-Ethyl-2-methyl-2-(3-methylbutyl)-1,3-oxazolidine Mixture D,L-2-Amino-1-butanol (AB ®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 5-methyl-2-hexanone (MIAK) (188.4 grams; 1.6 mol.) was added over a four minute period causing a four degree lowering of the reaction mixture temperature (22° C.→18° C.). The reaction mixture was heated to reflux and 21 grams of water were collected in the Dean-Stark trap over a twelve hour period. The crude product was purified by vacuum distillation (46°–48° C.@0.3 mm Hg) using a mirrored column (250 mm × 10 mm i.d.) packed with metal helixes. The material was stored under a nitrogen atmosphere.

Example 10

Preparation of 2-(1-Hydroxy-2-hydroxymethylbutyl)(5-methyl-2-hexylidine) amine/4-Ethyl-4-hydroxymethyl-2-methyl-2-(3-methylbutyl)- 1,3-oxazolidine Mixture 2-Amino-2-ethyl-1,3-propanediol (AEPD ®) (179.3 grams; 1.3 mol.)was added to a 3-neck, 1 liter round bottom flask equipped with a mechanical stirrer, a 500 ml addition funnel, a thermometer, and a Dean-Stark trap (100 ml capacity). While stirring, 5-methyl-2-hexanone (MIAK) (360.0 grams; 3.1 mol.) was added over a three minute period causing a one degree temperature drop in the reaction mixture temperature (22° C.→21° C.). The reaction mixture was heated to reflux and 25 grams of water were collected in the Dean-Stark trap over a ten hour period. The crude product was purified by vacuum distillation (98°–99° C.@0.3 mm Hg) using a mirrored column (250 mm × 10 mm i.d.) packed with metal helixes. The material was stored under a nitrogen atmosphere.

Example 11

Preparation of 2-(1-Hydroxybutyl)(2,6-dimethyl-4-heptylidine) amine/2,2-(Di-2-methylpropyl)-4-ethyl-1,3-oxazolidine Mixture D,L-2-Amino-1-butanol (AB ®) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). While stirring, 2,6-dimethyl-4-heptanone (DIBK) (234.7 grams; 1.3 mol.) was added over a two minute period causing a three degree lowering of the reaction mixture temperature (24° C.→21° C.). The reaction mixture was heated to reflux and 24 grams of water were collected in the Dean-Stark trap over a twenty hour period. The crude product was purified by vacuum distillation (95°–99° C.@1.5–1.8 mm Hg) using a mirrored column (250 mm × 10 mm i.d.) packed with metal helixes. The material was stored under a nitrogen atmosphere.

Example 12

Preparation of 2-(1-Hydroxy-2-methylpropyl)(4-methyl-2-pentylidine) amine/2-(2-Methylpropyl)-2,4,4-trimethyl-1,3-oxazolidine Mixture 2-Amino-2-methyl-1-propanol (AMP TM) (133.7 grams; 1.5 mol.) was added to a 3-neck, 500 ml round bottom flask equipped with a magnetic stir bar, a 250 ml addition funnel, a thermometer, and a Dean-Stark trap (50 ml capacity). The flask was warmed to 45° C. to melt the AMP TM. While stirring, 4-methyl-2pentanone (MIBK) (165.3 grams; 1.6 mol.) was added over a five minute period and the mixture was heated to reflux. After thirty-five hours, 23 grams of water were collected in the Dean-Stark trap. The crude product was purified by vacuum distillation (36° C.@1.1 mm Hg) using a mirrored column (250 mm × 10 mm i.d.) packed with metal helixes. The material was stored under a nitrogen atmosphere.

Example 13

Preparation of 2-(1,3-Dihydroxy-2-methylpropyl)(4-methyl-2-pentylidine) amine/4-Hydroxymethyl-2,4-dimethyl-2-(2-methylpropyl-1,3-oxazolidine Mixture 2-Amino-2-methyl-1,3-propanediol (AMPD TM) (157.7 grams; 1.5 mol.) was added to a 3-neck, 1 liter round bottom flask equipped with a mechanical stirrer, a 500 ml addition funnel, a thermometer, and a Dean-Stark trap (100 ml capacity). The flask was warmed to 115° C. to melt the AMPD TM. While stirring, 4-methyl-2-pentanone (MIBK) (180.3 grams; 1.8 mol.) was added gradually over a twenty-two minute period to prevent lowering the temperature and precipitation of the AMPD TM. The mixture was heated to reflux and after twenty-six hours, 24 grams of water were collected in the Dean-Stark trap. The crude product was purified by vacuum distillation (95° C.–100° C.@1.8–2.0 mm Hg) using a mirrored column (250 mm × 10 mm i.d.) packed with metal helixes. The material was stored under a nitrogen atmosphere.

Example 14

Preparation of 1-(2-Hydroxypropyl(5-methyl-2-hexylidine) amine/2,5-Dimethyl-2-(3-methylbutyl)-1,3-oxazolidine Monoisopropanolamine (MIPA) (118.6 grams; 1.58 mol.) was added to a 3-neck, 500 ml round bottom flask equipped with a mechanical stirrer, a 125 ml addition funnel, a thermometer, and a Dean-Stark trap (20 ml capacity). While stirring, 5-methyl-2-hexanone (MIAK) (202.4 grams; 1.76 mol.) was added over a 5 minute period causing a lower reaction mixture temperature. The reaction mixture was heated to reflux and 29 grams of water were collected in the Dean-Stark trap over a 2 hour period. The product was purified by vacuum distillation (85° C.–90° C.@15 mm Hg) using a mirrored column (250 mm×10 mm i.d.) packed with metal helixes. The material was stored under a nitrogen atmosphere.

Example 15

Preparation of 3-ethyl-2-methyl-2-(3-methylbutyl)-1,3-oxazolidine

In a 3 liter, 4-necked round bottom flask, equipped with a mechanical stirrer, a thermocouple, a glass column packed with Pro-Pak® packings, a dean-stark trap placed between the glass column and a Freidrich condenser, and a stopper, was added ethyl ethanolamine (EEA, 636.8 grams, 7.00 moles) under a nitrogen atmosphere. To this rapidly stirred EEA, methyl isoamyl ketone (MIAK, 12 11.3 grams, 10.5 moles) was added over a period of 5 minutes. The addition of MIAK was not significantly exothermic nor endothermic.

The resultant clear colorless solution was then heated to reflux to remove water azeotropically. This process took about 20 hours. During this period, reaction samples were taken and analyzed by GC to monitor the process of this reaction. A total of 121.9 grams of water was removed.

After this step, the reaction mixture was cooled to room temperature and the Dean-Stark trap was replaced with a distilling head and a receiver. Vacuum stripping (20 mm-Hg) of the lights (mainly MIAK and some EEA) was started. The vacuum stripping took about 5–6 hours. A total of 720.53 grams of precut was obtained and the residue contained >98% of 3-ethyl-2-methyl-2-(3-methylbutyl)-1,3-oxazolidine (GC area %).

The receiver was then changed and the product was flash distilled under vacuum (20 mm-Hg). A colorless, clear distillate 941.5 grams (boiling point range 90°–95° @20 mm-Hg) was obtained. Example 16
Reduction of Bubbles and Pinholes A two-component, high gloss general industrial coating based on HDI with a polyester polyol was formulated with and without 3-ethyl-2-methyl-2-(3-methylbutyl)-1,3-oxazolidine. Panels were sprayed and cured under procedures similar to the downglossing test of Example 17.

| Two-Component High Gloss Polyurethane Coating | |
|---|---|
| | Wt. % |
| COMPONENT 1 | |
| Polyester Polyol | 25.37 |
| Ketone/Ester Solvent Blend | 26.87 |
| Titanium Dioxide | 20.74 |
| Additives | 0.49 |
| Dibutyl Tin Dilaurate | 0.01 |
| 3-ethyl-2-methyl-2-(3-methylbutyl)-1,3-oxazolidine | 3.50 |
| COMPONENT 11 | |
| HDI Trimer | 23.02 |
| Total | 100.00 |
| Typical Properties | |
| VOC: | 2.8 lb./gal. 340 g/l |
| Density: | 10.01 lb./gal. 1199 g/l |
| Solids (by weight): | 72.04% |

Figure 1A:
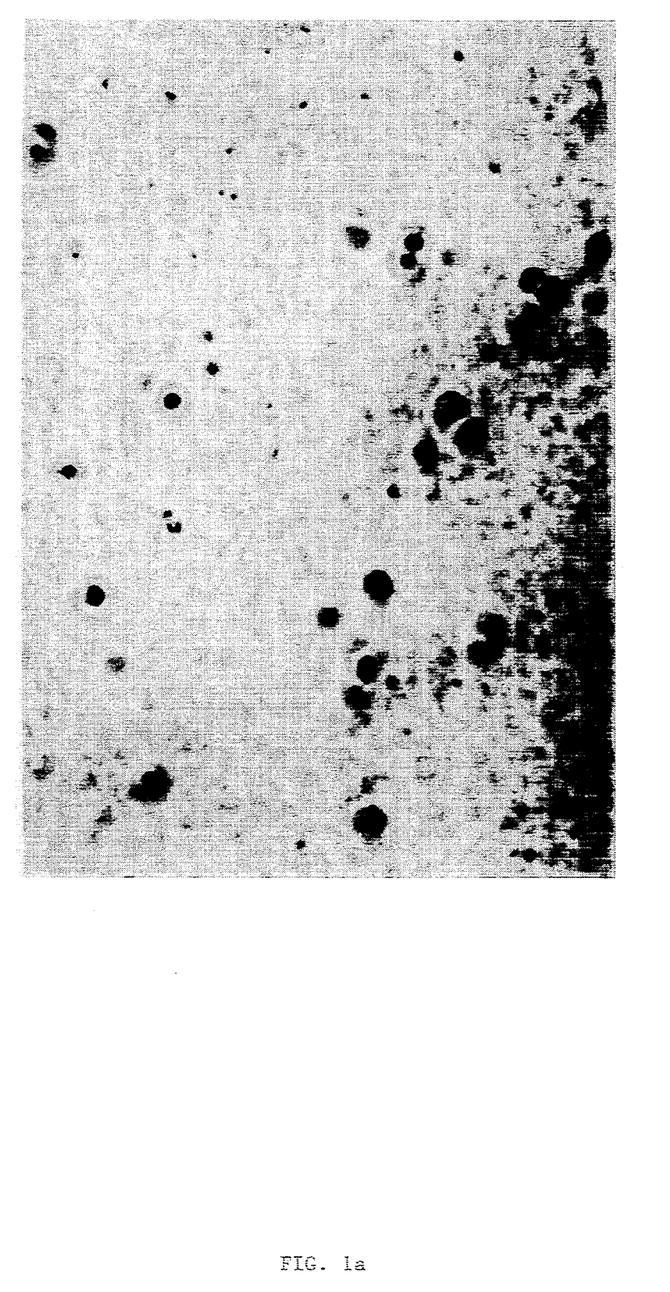
FIG. 1a is a photomicrograph of a polyurethane coating to which 3-ethyl-2-methyl-2-(3-methylbutyl)-1,3-oxazolidine has not been added.
Figure 1B:
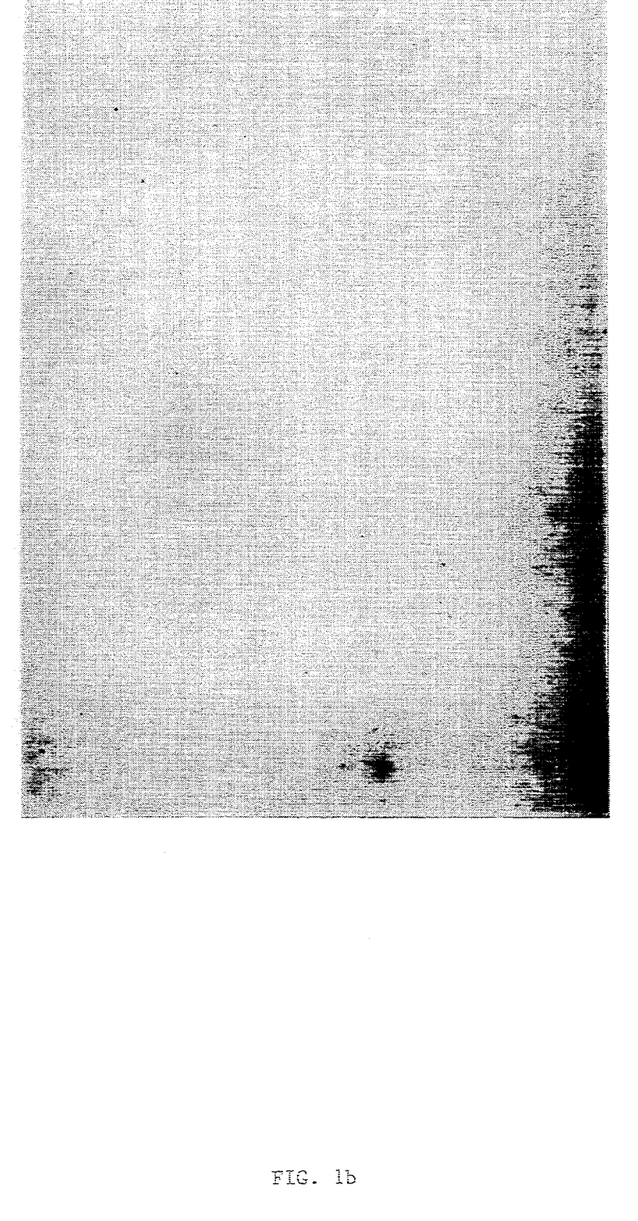
FIG. 1b is a photomicrograph of a polyurethane coating to which 3-ethyl-2-methyl-2-(3-methylbutyl)-1,3-oxazolidine has been added to reduce bubble formation.

As FIGS. 1a and 1b (photomicrographs) illustrate, the addition of 3-ethyl-2-methyl-2-(3-methylbutyl)1,3-oxazolidine to the system eliminated bubbles and pinholes in this high solids two-component polyurethane coating.

Example 17

Downglossing Study

A two-component medium gloss general industrial coating based upon HDI with a polyester polyol was formulated with and without 3-ethyl-2-methyl-2-(3-methylbutyl)-1,3-oxazolidine.

| Two-Component Polyurethane Coating | |
|---|---|
| | Wt. % |
| COMPONENT 1 | |
| Polyester Polyol | 16.95 |
| n-Butyl Acetate/MEK/Toluene | 11.86 |
| Antisettling/Dispersant/Flow-control Agent | <0.85 |
| Titanium Dioxide | 8.50 |
| Color Pigments | 1.27 |
| Fillers/Flatting Agents | 6.35 |
| Anti-mar Agent | <0.40 |
| Catalysts | <2.00 |
| UV Absorbers | <0.40 |
| 3-ethyl-2-methyl -2-(3-methylbutyl)-1,3-oxazolidine | 2.53 |
| COMPONENT 11 | |
| n-Butyl Acetate/MEK/Toluene | 5–15 |
| HDI Polyisocyanate | 35–45 |
| Typical Properties | |
| VOC: | 3.5 lb/gal., 450 g/l |
| Pigment/Binder Ratio | 0.34 |
| Density: | 10.3 lb/gal. |
| Solids (by Weight): | 66.02% |

Panels were sprayed at various temperatures and relative humidity to 1.7–2.3 mils dry. The panels were allowed to cure for 4–5 hours at these conditions and then dried overnight at 70° F. and 60% relative humidity. The following table shows the results of adding 3-ethyl-2-methyl-2-(3-methylbutyl)-1,3-oxazolidine to the system with the subsequent minimization of downglossing. The data in the following table shows that at high temperature and high humidity (90° F./85% Relative Humidity), the gloss value of a polyurethane coating is almost doubled by the addition of 3-ethyl-2-methyl-2-(3-methylbutyl)-1,3-oxazolidine to the urethane coating.

| Downglossing/Air Dry Two-Component Medium Gloss General Industrial Coating | | | | |
|---|---|---|---|---|
| | 60° Gloss Value | | 85° Gloss Value | |
| Conditions | Control | Example 17 Oxazolidine | Control | Example 17 Oxazaolidine |
| 70° F./60% Relative Humidity | 33 | 36 | 73 | 77 |
| 90° F./75% Relative Humidity | 31 | 35 | 65 | 73 |
| 90° F./85% Relative Humidity | 16 | 29 | 36 | 68 |

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims. Any $R_7$ group which can activate a ring opening, such as an ethyl group or an amine, aldimine or ketimine containing group, is preferred. Any R group substituents which increase the reactivity of a compound of the present invention to formaldehyde are within the scope of the present invention. For example, alkenyl and alkynl groups or substituent R groups may be selected as R group substituents if these groups increase the reactivity of the compound to formaldehyde. Likewise, any R group substituents which increase the reactivity of a reactive diluent compound to the active material whose concentration is to be reduced are within the scope of the present invention. Additionally, any R group substituents which improve the ability of a compound of the present invention to lower the freezing point of a preparation, provide improved solvency or pigment dispersability in a dispersion, suspension or solution, reduce the viscosity and improve the rheological properties of a preparation, or remove the color from a preparation are also preferred.

We claim:

1. A method of reducing bubble formation in a polyurethane coating, wherein the method comprises admixing with the polyurethane at least one mole of a bubble-reducing agent for every mole of water in the polyurethane coating, the bubble-reducing agent being selected from the group consisting of:

an iminoalcohol compound having the structure:

(I)

an oxazolidine compound having the structure:

(II)

and a mixture of the iminoalcohol compound and the oxazolidine compound wherein; $R_1$ and $R_2$ are, individually, selected from the group consisting of a methyl or methylol group, an ethyl group, and a branched or straight chain alkyl or alkanol group; $R_3$, $R_4$ and $R_5$ are, individually selected from the group consisting of a hydrogen atom, a methyl or methylol group, and ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

2. A method of reducing downglossing in a polyurethane coating, wherein the method comprises admixing with the polyurethane at least one mole of a downglossing reduction agent for every mole of water in the polyurethane coating, the downglossing reduction agent being selected from the group consisting of:

an iminoalcohol compound having the structure:

(I)

an oxazolidine compound having the structure:

(II)

and a mixture of the iminoalcohol compound and the oxazolidine compound wherein: $R_1$ and $R_2$ are, individually selected from the group consisting of a methyl or methylol group, an ethyl or ethylol group, and a branched or straight chain alkyl or alkanol group; $R_3$, $R_4$ and $R_5$ are, individually, selected from the group consisting of a hydrogen atom, a methyl or methylol group, an ethyl or ethylol group, and a straight chain or branched chain alkyl or alkanol group; $R_6$ is selected from the group consisting of a hydrogen atom, a methyl group, an ethyl group, and a straight chain or branched chain alkyl group; and $R_7$ is selected from the group consisting of a hydrogen atom, a methyl or methylol group, an ethyl or ethylol group, a straight chain or branched chain alkyl or alkanol group, a cycloalkyl group, an acyl group and an aryl group, and wherein the concentration of the iminoalcohol compound is from 0 to 100 mole percent and the concentration of the oxazolidine compound is from 0 to 100 mole percent.

* * * * *